US008617088B2

(12) United States Patent
Samuelsson et al.

(10) Patent No.: US 8,617,088 B2
(45) Date of Patent: Dec. 31, 2013

(54) MEDICAL GUIDE WIRE ASSEMBLY

(75) Inventors: Magnus Samuelsson, Uppsala (SE);
Antonia Cornelia van Rens, Gerwen (NL)

(73) Assignees: St. Jude Medical Systems AB, Uppsala (SE); Koninklijke Philips Electronics N.V., Eindhoven (NL)

( * ) Notice: Subject to any disclaimer, the term of this patent is extended or adjusted under 35 U.S.C. 154(b) by 347 days.

(21) Appl. No.: 13/016,120

(22) Filed: Jan. 28, 2011

(65) Prior Publication Data
US 2011/0213220 A1 Sep. 1, 2011

Related U.S. Application Data

(60) Provisional application No. 61/299,481, filed on Jan. 29, 2010.

(51) Int. Cl.
*A61B 5/00* (2006.01)
(52) U.S. Cl.
USPC ........................................................ 600/585
(58) Field of Classification Search
USPC ............................................ 600/561, 585, 587
See application file for complete search history.

(56) References Cited

U.S. PATENT DOCUMENTS

| | | | |
|---|---|---|---|
| 5,199,108 | A | 3/1993 | Morgan et al. |
| 5,564,434 | A | 10/1996 | Halperin et al. |
| 5,593,430 | A * | 1/1997 | Renger ........................... 607/18 |
| RE35,648 | E | 11/1997 | Tenerz et al. |
| 6,106,486 | A | 8/2000 | Tenerz et al. |
| 6,182,513 | B1 | 2/2001 | Stemme et al. |
| 6,343,514 | B1 | 2/2002 | Smith |

(Continued)

FOREIGN PATENT DOCUMENTS

| | | |
|---|---|---|
| EP | 1 800 597 A2 | 6/2007 |
| EP | 1 849 409 A1 | 10/2007 |
| EP | 1 927 314 A1 | 6/2008 |
| WO | WO 00/30534 A1 | 6/2000 |

OTHER PUBLICATIONS

U.S. Appl. No. 13/016,201, filed Jan. 28, 2011, Samuelson et al.

(Continued)

*Primary Examiner* — Max Hindenburg
(74) *Attorney, Agent, or Firm* — Foley & Lardner LLP

(57) ABSTRACT

Medical guide wire assembly comprising a guide wire having a proximal end and a distal end, at least one physiology parameter sensor, and that the proximal end of the guide-wire is provided with an elongated connector part, having connection electrodes, for insertion into a connector housing provided with an elongated tubing adapted to achieve electrical and mechanical connection to the elongated connector part, the connector housing is in its turn electrically or wirelessly connectable to a physiology monitor. The guide wire is provided with a core wire running essentially along the entire guide wire. A sensor signal processing circuitry is arranged in connection with the physiological sensor and is adapted to generate a processed sensor signal in response of a sensed parameter. The sensor signal processing circuitry comprises a modulation unit arranged to modulate the processed sensor signal and to generate a modulated sensor signal. The assembly comprises exactly two micro-cables that are connected to the sensor signal processing circuitry, the micro-cables run along the guide wire and are connected to the connection electrodes of the connector part, wherein one of the core wire and the two micro-cables are actively used when transferring the processed and modulated sensor signal to the connector housing.

21 Claims, 4 Drawing Sheets

(56) References Cited

U.S. PATENT DOCUMENTS

| | | |
|---|---|---|
| 6,461,301 B2 | 10/2002 | Smith |
| 6,615,067 B2 | 9/2003 | Hoek et al. |
| 6,626,852 B2 | 9/2003 | White et al. |
| 6,692,446 B2 | 2/2004 | Hoek |
| 7,194,297 B2 | 3/2007 | Talpade et al. |
| 2001/0045899 A1 | 11/2001 | Hoek |
| 2005/0096562 A1 | 5/2005 | Delalic et al. |
| 2006/0009817 A1 | 1/2006 | Tulkki |
| 2007/0055098 A1 | 3/2007 | Shimizu et al. |
| 2007/0255144 A1 | 11/2007 | Tulkki et al. |

OTHER PUBLICATIONS

USPTO Office Action U.S. Appl. No. 13/016,201, May 24, 2013, 10 pages.

\* cited by examiner

MEDICAL GUIDE WIRE ASSEMBLY

FIELD OF THE INVENTION

The present invention relates to a medical guide wire assembly according to the preamble of the independent claim.

BACKGROUND OF THE INVENTION

The present invention relates generally to sensor and guide wire assemblies, in which one or many sensors is/are mounted preferably at the distal end of a guide wire for intravascular measurements of physiological variables in a living body, and in particular in relation to the communication with the sensor(s).

Sensor and guide wire assemblies in which a sensor is mounted at the distal end of a guide wire are known. In U.S. Pat. No. Re. 35,648, which is assigned to the present assignee, an example of such a sensor and guide wire assembly is disclosed, where a sensor guide comprises a sensor element, an electronic unit, a signal transmitting cable connecting the sensor element to the electronic unit, a flexible tube having the cable and the sensor element disposed therein, a solid metal wire (also called a core wire), and a coil attached to the distal end of the solid wire. The sensor element comprises a pressure sensitive device, e.g. a membrane, with piezoresistive elements connected in a Wheatstone bridge-type of arrangement mounted thereon. An exemplifying electrical circuit arrangement can also be found in the present applicant's U.S. Pat. No. 6,343,514. As an alternative, the pressure sensitive device can also be in the form of a resonant structure, as is disclosed in the present applicant's U.S. Pat. Nos. 6,182,513 and 6,461,301. Instead of using cables to connect a sensor element to an electronic unit, other ways of receiving sensor signals can be employed. U.S. Pat. Nos. 6,615,067 and 6,692,446, which are assigned to the present assignee, disclose sensor systems for signal transmission via body tissues and passive biotelemetry, respectively.

Many different types of sensors are illustrated in the cited prior art, and many are based upon the piezoresistive effect where the changing of electrical resistance of a material is due to applied mechanical stress. The piezoresistive effect differs from the piezoelectric effect. In contrast to the piezoelectric effect, the piezoresistive effect only causes a change in resistance, it does not produce electrical charges. Piezoresistors are resistors made from a piezoresistive material and are usually used for measurement of mechanical stress. They are the simplest form of piezoresistive devices.

Thus, the above sensors are passive sensors where a physiological variable is sensed and transmitted directly as a resistance, a current, a voltage, etc. being representative of physiological variable.

Normally, the sensor is powered by a separate micro cable and the sensor signal is transmitted from the sensor to the proximal end of the guide wire via two other micro cables for further processing by a connected processing unit.

Signal transmission from such sensors may be hampered by cable/connector effects, e.g. cable resistance temperature coefficients, contact resistance, leakage due to wetting etc. and bending and mechanical strain on the wire causes disturbances.

If multiple sensors are to be used each sensor requires a separate set of micro cables, and if multiple cable strands and connector elements are used they may severely limit the mechanical performance of a guide wire, and in addition they are difficult to manufacture and are thus prone to reliability issues.

The object of the present invention is to achieve an guide wire assembly that obviates the above drawbacks related to guide wires provided with numerous micro cables, in particular in multi sensor arrangements.

SUMMARY OF THE INVENTION

The above-mentioned object is achieved by the present invention according to the independent claim.

Preferred embodiments are set forth in the dependent claims.

Thus, according to the invention the guide wire assembly requires only two micro cables which is advantageous in many aspects.

The manufacture is simplified, e.g. it is easier to connect the micro cables to the circuitry chip in that it allows for much easier wire-to-chip bonding, it reduces the number of contact elements in the proximal connector and reduces complexity of wire fabrication. In addition the guide wire tubing that encloses the core wire along the guide wire may then be differently arranged, it could e.g. have a thicker wall.

According to a first embodiment the core wire is used as an active signalling channel, i.e. the processed and modulated sensor signal is submitted via the core wire. The signalling is preferably bidirectional, i.e. both from the sensor and active circuitry to the readout system and vice versa.

A presumption for using the core wire as an active signalling part is that the inherent capacitances are handled which exist between the micro cables and the core wire along the entire guide wire. That may be achieved by arranging an inductance in order to achieve reactance matching. The theoretical circuitry of capacitance and inductance will then have a resonance frequency, i.e. a frequency that is amplified, and the processed sensor signal to be supplied via the core wire may then use that frequency.

The signal processing of the sensor signal must then be performed in the sensor circuitry and the processed sensor signal is preferably a high frequency (MHz) AC voltage, having no DC level.

A further advantage by this arrangement is that numerous sensors may be arranged along the guide wire as the sensor signals may be transferred simultaneously as they e.g. use different frequency.

The signalling through the core wire may have both DC and AC components although using only AC components with capacitive coupling has several advantages such as:

Improved safety for unwanted leakage currents.

Multiple sensors can readily be used on the same wire.

Maintains signal waveform despite capacitive loading of the wire.

"Isolates" capacitive loading from the wire from the signal driver output stage thus limiting excessive drive currents.

According to a second embodiment the power supply and the active signalling channel use one of the micro cables and the other micro cable is used as ground. In this embodiment the sensor signal is superimposed a DC level used as power supply.

Also in this embodiment the signal processing of the sensor signal must be performed in the sensor circuitry and the processed sensor signal is preferably a high frequency (MHz) AC voltage.

A further advantage by the arrangement according to this second embodiment is also, as in the first embodiment, that numerous sensors may be arranged along the guide wire as the sensor signals may be transferred simultaneously as they use e.g. different frequency.

SHORT DESCRIPTION OF THE APPENDED DRAWINGS

Figures 1, 3:
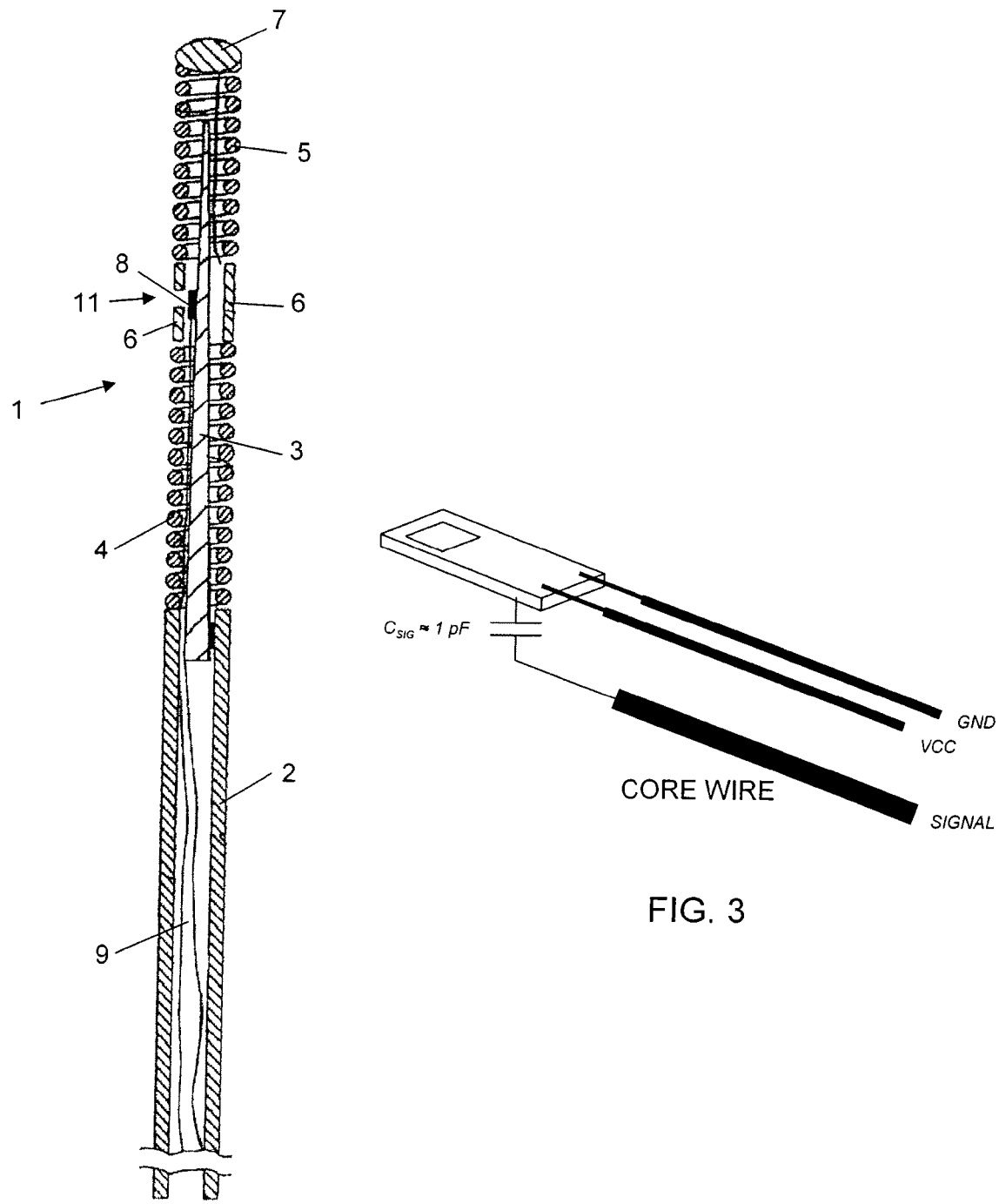
FIG. 1 illustrates a conventional sensor and guide wire assembly.

FIG. 3 schematically illustrates the sensor chip and connected micro cables according to a first embodiment.

Figure 4:
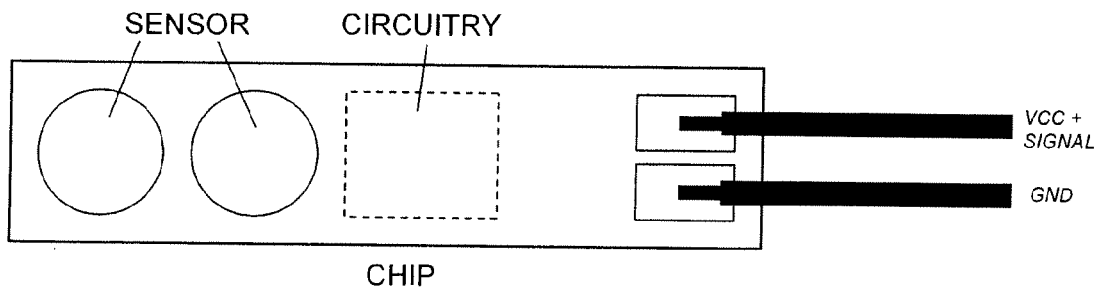

FIG. 4 schematically illustrates the sensor chip and connected micro cables according to a second embodiment.

Figure 5:
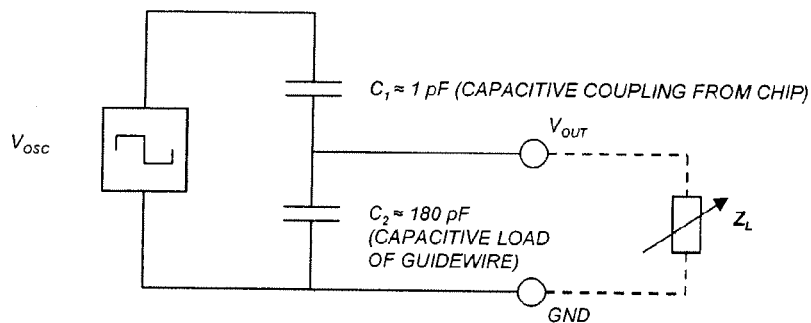

FIG. 5 shows a simplified electrical circuit representing the capacitive situation of the guide wire.

Figure 6:
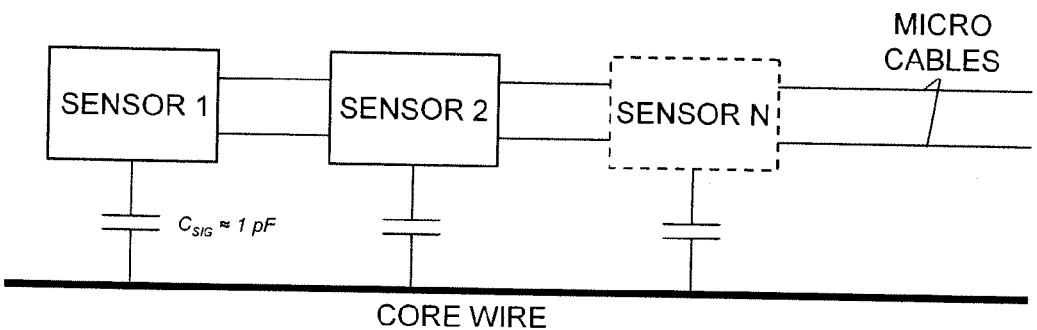

FIG. 6 schematically illustrates a multi sensor guide wire assembly according to the present invention.

Figure 7:
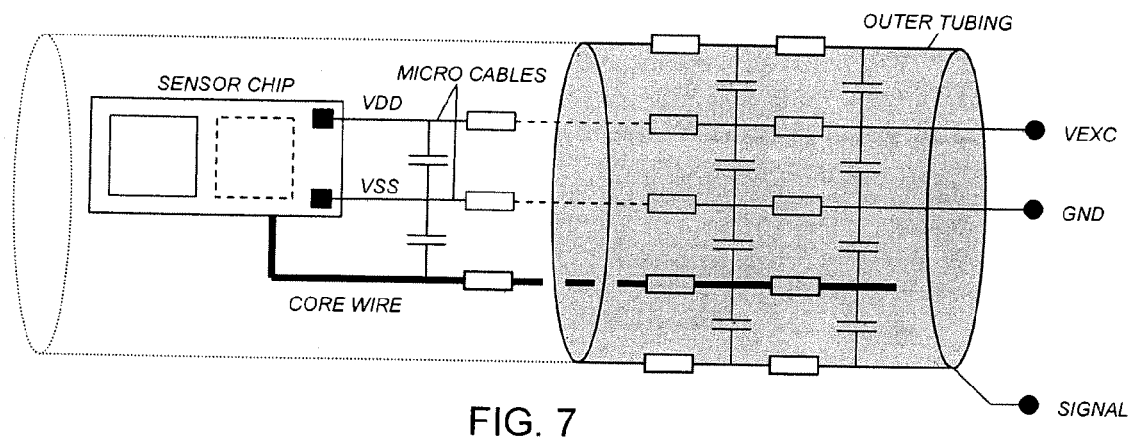
Figure 8:
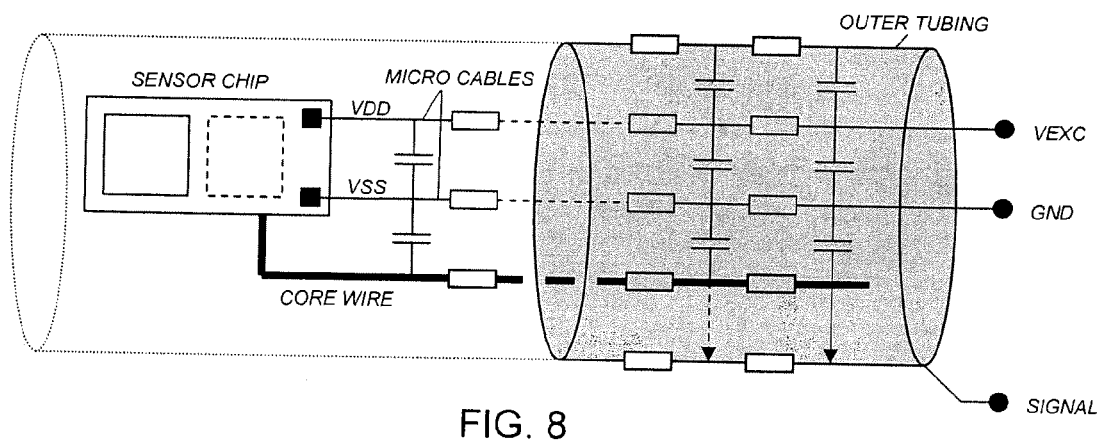

FIGS. 7 and 8 schematically illustrate resistances and capacitances along the guide wire.

Figure 9:
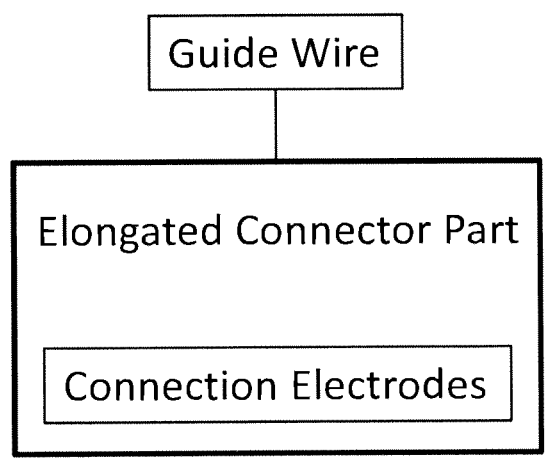

FIG. 9 is a block diagram showing the guide wire and an elongated connector part having connection electrodes.

DETAILED DESCRIPTION OF PREFERRED EMBODIMENTS OF THE INVENTION

For better understanding of the context in which a sensor according to the present invention is going to be used, a sensor and guide wire assembly 1 of a conventional design is illustrated in FIG. 1. The sensor guide 1 comprises a hollow tube 2, a core wire 3, a first coil 4, a second coil 5, a jacket or sleeve 6, a dome-shaped tip 7, a sensor element 8, and one or several electrical leads 9. The proximal end of the first coil 4 is attached to the distal end of the hollow tube 2, while the distal end of the first coil 4 is attached to the proximal end of the jacket 6. The proximal end of the second coil 5 is connected to the distal end of the jacket 6, and the dome-shaped tip 7 is attached to the distal end of the second coil 5. The core wire 3 is at least partly disposed inside the hollow tube 2 such that the distal portion of the core wire 3 extends out of the hollow tube 2 and into the second coil 5. The sensor element 8 is mounted on the core wire 3 at the position of the jacket 6, and is through the electrical leads 9 connected to an electronic unit (not shown in the figure). The sensor element 8 comprises a pressure sensitive device in the form of a membrane (not visible in the figure), which through an aperture 11 in the jacket 6 is in contact with a medium, such as blood, surrounding the distal portion of the sensor guide 1. As is well known in the art, the dimensions as well as other properties of guide wires adapted for introduction into the artery can vary considerable based on the type of procedure being performed, the particular patient, etc. The corresponding ranges of dimensions are also applicable to a sensor guide whose distal end is provided with a sensor element. In one conventional design of a sensor guide like the sensor guide 1 shown in FIG. 1, the diameter of the tube 2 is about 0.014 inches (0.36 mm) and the dimensions of element 8 are 1340×180×100 μm (length× width×height).

Although not shown in the figure, the sensor element 8 further comprises an electrical circuitry, which in a Wheatstone bridge-type of arrangement is connected to one or several piezoresistive elements provided on the membrane. As is well known in the art, a certain pressure exerted on the membrane from the surrounding medium will thereby correspond to a certain stretching or deflection of the membrane and thereby to a certain resistance of the piezoresistive elements mounted thereon and, in turn, to a certain output from the sensor element 8.

Figure 2:
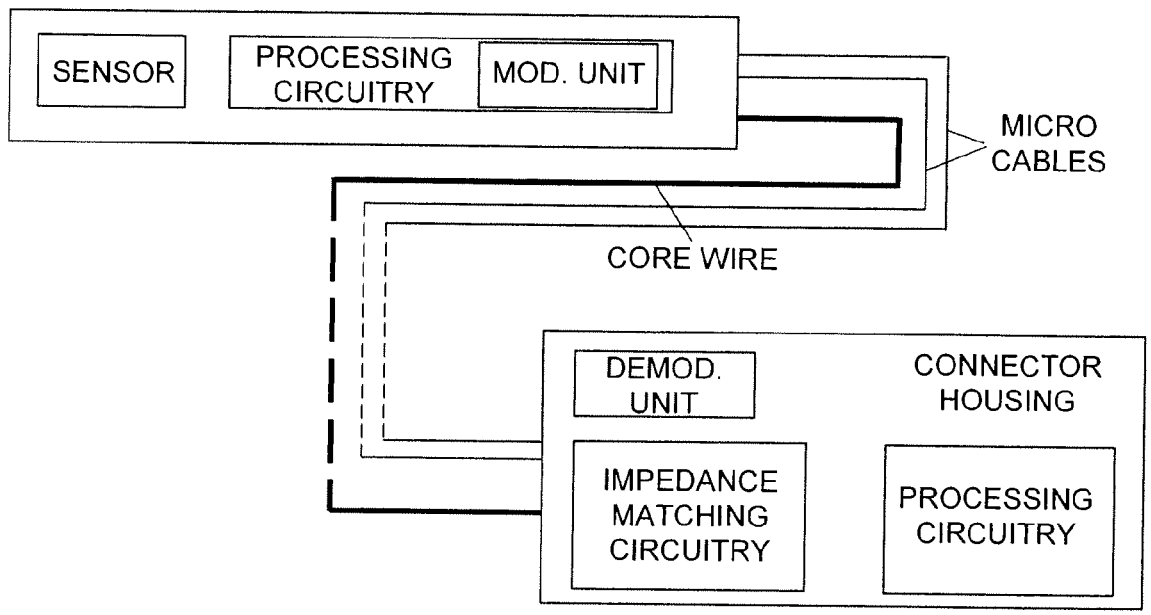
FIG. 2 is a schematic illustration of a sensor guide wire assembly according to the present invention.

With references to FIG. 2 the medical guide wire assembly according to the present invention will now be described in detail.

The medical guide wire assembly comprises a guide wire having a proximal end and a distal end, and is preferably of the type shown in FIG. 1 and is provided with at least one physiology parameter sensor, e.g. a pressure sensor. The sensor is preferably arranged close to the distal end. The proximal end of the guide-wire is provided with an elongated connector part, having connection electrodes, for insertion into a connector housing provided with an elongated tubing adapted to achieve electrical and mechanical connection to the elongated connector part, the connector housing is in its turn electrically or wirelessly connectable to a physiology monitor (not shown). The guide wire is further provided with a core wire running essentially along the entire guide wire, and a sensor signal processing circuitry, arranged in connection with the physiological sensor, and adapted to generate a processed sensor signal in response of a sensed parameter. An outer tubing, or hollow tube, (not shown) encloses the core wire essentially along the entire guide wire.

The sensor signal processing circuitry comprises a modulation unit arranged to modulate the processed sensor signal and to generate a modulated sensor signal. The assembly also comprises exactly two micro-cables that are connected to the sensor signal processing circuitry, and that the micro-cables run along the guide wire inside the outer tubing and are connected to the connection electrodes of the connector part.

One of the core wire and the two micro-cables is actively used when transferring the processed and modulated sensor signal to the connector housing.

The sensor and the signal processing circuitry is preferably arranged at a circuitry chip.

Two main embodiments may be identified of the assembly using only two micro cables, i.e. how the signalling is performed and how the sensor chip is power supplied.

In the first embodiment of the guide wire assembly the core wire is used to transfer the modulated sensor signal, i.e. being the active channel, one of the micro-cables is used for power supply of the circuitry and the other micro-cable is used as ground. This embodiment is illustrated in FIG. 3.

In order to secure safe signalling an impedance matching circuitry is arranged in the connector housing to take care of impedances between the core wire and the tubing. Two different alternatives are available, in one alternative the core wire is covered at its surface by an insulating layer, e.g. Teflon or a polymer, that may serve two purposes, to electrically isolate the core wire from the tubing and to reduce the friction between the core wire and the tubing. This two alternatives are schematically illustrated in the electrical representations of the guide wire shown in FIGS. 7 and 8, where FIG. 7 shows a so-called floating core wire, i.e. the core wire provided with coating, and FIG. 8 shows a so-called connected core wire, i.e. the core wire is not provided with a coating and may then be in electrical contact with the tubing.

FIGS. 7 and 8 illustrate resistances and capacitances along the guide wire, which form basis for tuning the impedance matching circuitry that is electrically connected to the core wire and the micro-cables to match the impedance of the core wire and micro cable(s), and includes preferably at least one tuning inductor.

FIG. 5 shows a simplified electrical circuit representing the capacitive situation of the guide wire and a connected impedance matching circuitry $Z_L$. By adding an external impedance ($Z_L$) with inductive behaviour a circuit is formed that is tuned with the capacitive behaviour of the guide wire, which will result in a higher signal output despite a relatively low oscillator driver stage amplification of the sensor signal in the sensor chip. In addition the resistance to electromagnetic interference (EMI) is improve as a sinusoidal signal may be used when transmitting the sensor signal. In the set-up illustrated in FIG. 5 the output signal $V_{out}=V_{osc} \cdot C_1/(C_1+C_2)$, where $V_{osc}$ is the amplitude to the oscillator used to modulate the sensor signal, $C_1$ is the capacitive coupling from the chip, in this example approx. 1 pF, and $C_2$ is the capacitive load of the guide wire, in this example approx. 180 pF. $Z_L$ may e.g. be realized by an inductor or other means (a gyrator etc).

By controlling Q for the impedance matching circuitry the amplification and bandwidth may be tailored to suit the modulation chosen. $Z_L$ may be tuneable to track the signal frequency and/or allow for variations in guide wire capacitive behaviour.

In the second embodiment, which is illustrated by FIG. 4, one of the micro cables is used as power supply of the sensor chip(s) and for signalling purposes and the other micro cable is used as ground.

In this embodiment the sensor signal is superimposed on the power supply DC voltage. This embodiment may require large on-chip capacitors (or voltage regulators) at the sensor circuitry chip. The signalling is preferably bidirectional, i.e. both from the sensor and active circuitry to the readout system and vice versa.

The signalling between the signal processing circuitry and the processing circuitry of the connector housing is performed by the modulated sensor signal which is transferred by using a multiple access technique According to three different embodiments the multiple access technique is a frequency division multiple access technique, a time division multiple access technique, or a code division multiple access technique.

To achieve the modulation, the modulation unit preferably includes an oscillator adapted to generate a modulated sensor signal having a variable frequency, amplitude, or duty cycle.

Alternatively, the modulation unit includes a sigma-delta modulator adapted to generate a modulated sensor signal including a bit stream.

In order to demodulate the received modulated signal the connector housing is provided with a demodulation unit adapted to demodulate the signal. The connector housing is also provided with a processing circuitry adapted to process the demodulated signal.

According to another embodiment the guide wire assembly comprises two or more physiology parameter sensors arranged along the guide wire. This embodiment is schematically illustrated in FIG. 6, where an assembly provided with n sensors is shown. Each sensor is provided with a dedicated sensor signal processing circuitry including a modulation unit adapted to process and modulate the sensor signal and to transfer the processed and modulated sensor signal to the connector housing.

The sensor signals from all sensors are transferred at the same actively used channel, e.g. the core wire or one of the micro-cables, i.e. the multi sensor guide wire is applicable to both the first and second embodiment. In a multi sensor guide wire the sensors may include at least two of a pressure sensor, a temperature sensor or a flow sensor, or any other type of sensor, where each sensor has different modulation schemes when using any of the multiple access techniques, e.g. Frequency Division Multiple Access, Time Division Multiple Access or Code Division Multiple Access.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A medical guide wire assembly comprising:
   a guide wire having a proximal end and a distal end, the guide wire comprising a core wire running essentially along the entire guide wire;
   at least one physiological parameter sensor;
   an elongated connector part at the proximal end of the guide wire, having connection electrodes, configured for insertion into a connector housing provided with an elongated tubing configured to achieve electrical and mechanical connection to the elongated connector part; and
   sensor signal processing circuitry arranged for connection with the at least one physiological parameter sensor configured to generate a processed sensor signal in response to a sensed parameter, wherein the sensor signal processing circuitry comprises a modulation unit arranged to modulate the processed sensor signal and to generate a modulated sensor signal;
   wherein the assembly includes exactly two micro-cables that are connected to the sensor signal processing circuitry, the micro-cables running along the guide wire and being connected to connection electrodes of the connector part, and
   wherein either (i) the core wire is configured to be actively used for transferring the processed and modulated sensor signal to the connector housing, or (ii) the two micro-cables are configured to be actively used for transferring the processed and modulated sensor signal to the connector housing.

2. A guide wire assembly according to claim 1, wherein the at least one physiological parameter sensor includes one sensor that is arranged close to the distal end of the guide wire.

3. A guide wire assembly according to claim 1, wherein the at least one physiological parameter sensor includes a pressure sensor.

4. A guide wire assembly according to claim 1, wherein the at least one physiological parameter sensor and the circuitry are arranged at a circuitry chip.

5. A guide wire assembly according to claim 1, wherein the modulated sensor signal is transferred by using a multiple access technique.

6. A guide wire assembly according to claim 5, wherein the multiple access technique is a frequency division multiple access technique.

7. A guide wire assembly according to claim 5, wherein the multiple access technique is a time division multiple access technique.

8. A guide wire assembly according to claim 5, wherein the multiple access technique is a code division multiple access technique.

9. A guide wire assembly according to claim 5, wherein the modulation unit includes an oscillator configured to generate a modulated sensor signal having a variable frequency, amplitude, or duty cycle.

10. A guide wire assembly according to claim 5, wherein the modulation unit includes a sigma-delta modulator configured to generate a modulated sensor signal including a bit stream.

11. A guide wire assembly according to claim 5, wherein the connector housing is provided with a demodulation unit configured to demodulate a received processed and modulated signal, and a processing circuitry configured to process the demodulated signal.

12. A guide wire assembly according to claim 5, wherein the assembly comprises two or more physiological parameter sensors arranged along the guide wire, and each of the two or more physiological parameter sensors is provided with a dedicated sensor signal processing circuitry including a modulation unit configured to process and modulate the respective sensor signal and to transfer the processed and modulated sensor signal to the connector housing.

13. A guide wire assembly according to claim 12, wherein all sensor signals are transferred at the same actively used channel.

14. A guide wire assembly according to claim 12, wherein the two or more physiological parameter sensors includes at least two sensors selected from the group consisting of a pressure sensor, a temperature sensor and a flow sensor.

15. A guide wire assembly according to claim 1, wherein the core wire is configured to transfer the modulated sensor signal and one of the micro-cables is configured for voltage supply of the circuitry and the other micro-cable is configured as ground.

16. A guide wire assembly according to claim 15, wherein an impedance matching circuitry is arranged in the connector housing to be electrically connected to the core wire and a micro-cable to match the impedance of the core wire and at least one micro-cable.

17. A guide wire assembly according to claim 16, wherein the impedance matching circuitry includes a tuning inductor.

18. A guide wire assembly according to claim 1, wherein one of the micro-cables is configured to transfer the modulated sensor signal and for voltage supply of the circuitry and the other micro-cable is configured as ground.

19. A medical guide wire assembly comprising:
a guide wire having a proximal end and a distal end, the guide wire comprising a core wire running essentially along the entire guide wire;
at least one physiological parameter sensor;
an elongated connector part at the proximal end of the guide wire, having connection electrodes, configured for insertion into a connector housing provided with an elongated tubing configured to achieve electrical and mechanical connection to the elongated connector part; and
sensor signal processing circuitry arranged for connection with the at least one physiological parameter sensor configured to generate a processed sensor signal in response to a sensed parameter, wherein the sensor signal processing circuitry comprises a modulation unit arranged to modulate the processed sensor signal and to generate a modulated sensor signal;
wherein the assembly includes exactly two micro-cables that are connected to the sensor signal processing circuitry, the micro-cables running along the guide wire and being connected to connection electrodes of the connector part, and
wherein the core wire is configured to be actively used for transferring the processed and modulated sensor signal to the connector housing.

20. A guide wire assembly according to claim 19, wherein the assembly comprises two or more physiological parameter sensors arranged along the guide wire, and each sensor is provided with a dedicated sensor signal processing circuitry including a modulation unit configured to process and modulate the respective sensor signal and to transfer the processed and modulated sensor signal to the connector housing.

21. A guide wire assembly according to claim 20, wherein all processed and modulated sensor signals are transferred by the core wire.

* * * * *